United States Patent [19]

Auer et al.

[11] 4,281,924
[45] Aug. 4, 1981

[54] REFLECTOR FOR THE LASER BEAM OF A PARTICLE ANALYZER

[75] Inventors: Robert E. Auer, South Miami; Wallace H. Coulter, Miami Springs, both of Fla.

[73] Assignee: Coulter Electronics, Inc., Hialeah, Fla.

[21] Appl. No.: 6,011

[22] Filed: Jan. 24, 1979

[51] Int. Cl.³ .................... G01N 21/49; G01N 21/64
[52] U.S. Cl. .................................. 356/73; 250/461 B; 356/318; 356/338
[58] Field of Search ................. 350/293, 296; 356/39, 356/73, 301, 317, 318, 337–343, 417; 250/461 R, 461 B

[56] References Cited

U.S. PATENT DOCUMENTS

| | | | |
|---|---|---|---|
| 3,398,286 | 8/1968 | Ford et al. | 356/338 X |
| 3,704,951 | 12/1972 | Chupp | 356/318 X |
| 3,807,862 | 4/1974 | Hatzenbuhler | 356/318 X |
| 4,022,529 | 5/1977 | White | 356/318 |
| 4,127,329 | 11/1978 | Chang et al. | 356/301 |

*Primary Examiner*—F. L. Evans
*Attorney, Agent, or Firm*—William A. Newton

[57] ABSTRACT

An apparatus and method for illuminating particles, wherein a source of illumination provides a beam of illuminating radiation which perpendicularly intersects a stream of liquid having the particles suspended therein. The illuminator apparatus comprises a concave reflector surface having a center of curvature and an optical axis which is disposed perpendicularly relative to the stream and with the beam being positioned thereon. The stream of liquid defines a cylindrical lens having a focus positioned at the center of curvature. In operation, the illuminating radiation illuminates the particles, is refracted by the stream so as to converge to a focus, passes from that focus to a concave reflector surface, and reflects from the concave reflector surface back to the focus, so as to impinge upon the stream for a second time, to further illuminate the particles.

10 Claims, 6 Drawing Figures

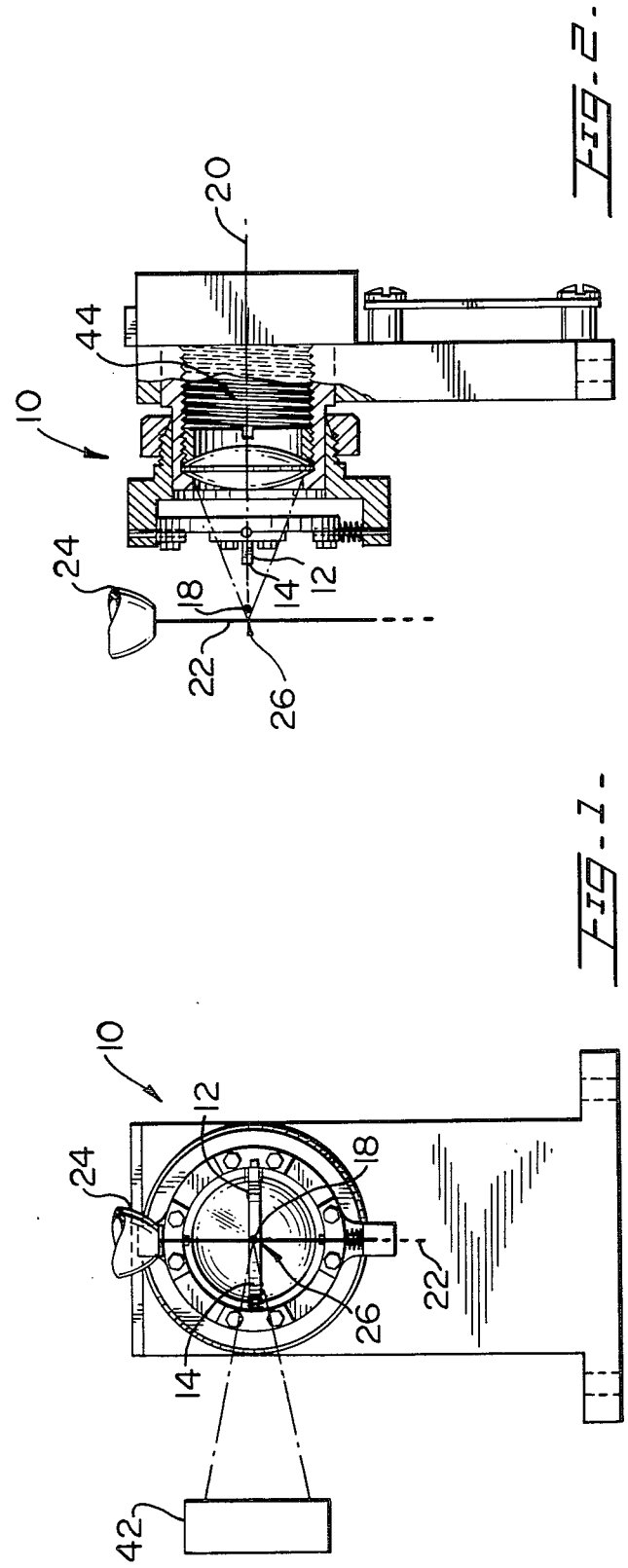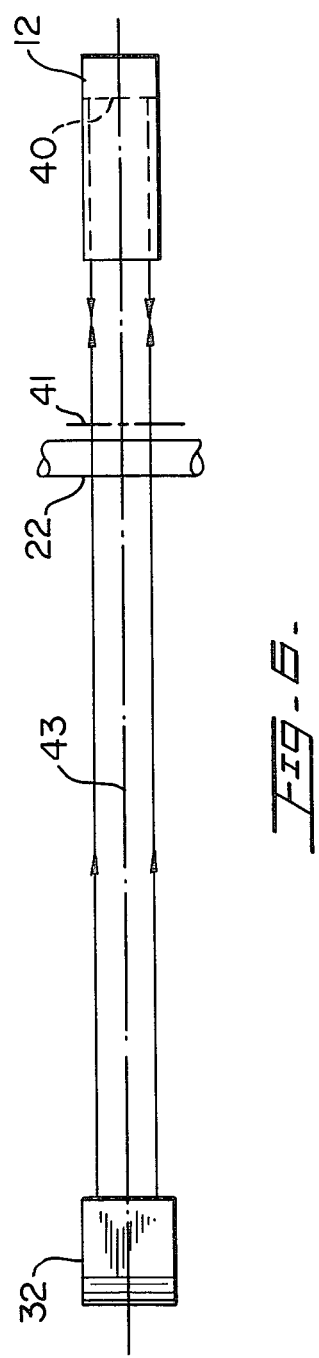

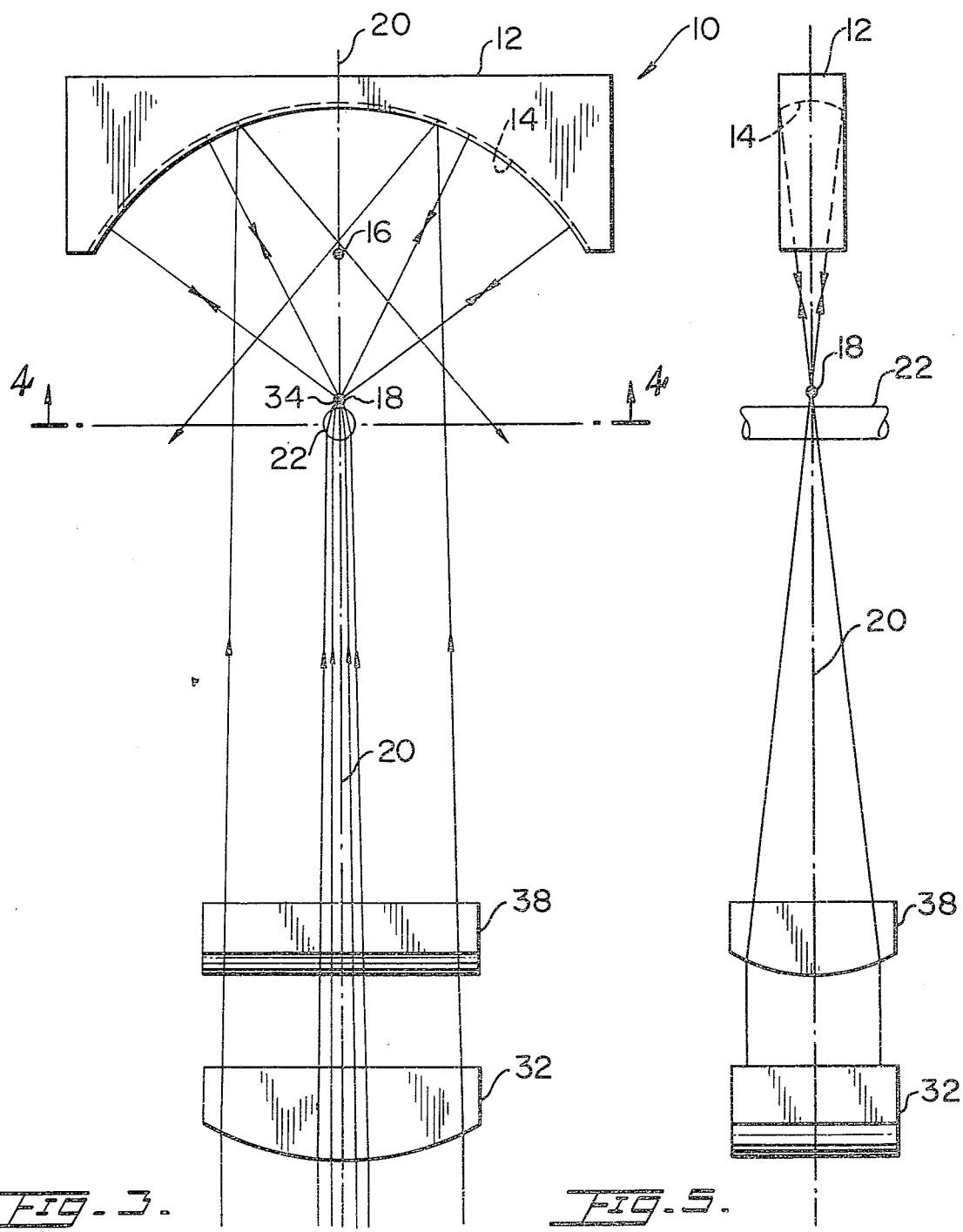
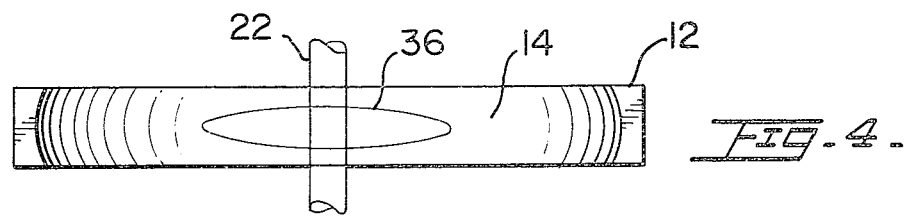

REFLECTOR FOR THE LASER BEAM OF A PARTICLE ANALYZER

FIELD OF THE INVENTION

The present invention relates to the illumination of individually isolated particles and more specifically, to the illumination by a substantially collimated laser beam of biological cells suspended in a liquid stream for the purpose of studying such cells.

BACKGROUND OF THE INVENTION

In the field of cytology, individual cells can be differentiated on the basis of quantitative and qualitative characteristics, one of these characteristics being the cell's staining behavior. In techniques which evaluate staining behavior, the cell constituents to be measured, for example, DNA, RNA, and protein, are tagged with fluorescent dyes which fluoresce when illuminated, while the rest of the cell remains relatively dark at the wavelength of the fluorescence. The intensity of the fluorescent light and the amount or type of cell constituent are correlated so as to provide a basis for analysis of collected data. Consequently, it is important that the collected fluorescent signal corresponds to the amount of non-homogeneously or homogeneously distributed fluorescent material contained within the cell and not be dependent upon the cell's orientation and/or position in the illuminating radiation. Therefore, it readily may be seen that uniformity of illumination of the fluorescent material within a given cell is essential to obtaining accurate and reliable results.

As has recently become appreciated, illumination of cells with relatively narrow beams of illuminating radiation, such as laser light, creates "hot spots", i.e., regions of relatively large energy density as compared to neighboring regions within the cell. In other words, regions of non-uniform radiation or "hot spots" represent uneven illumination so that all parts of a cell are not exposed to the same amount of energy. These "hot spots" are due to optical effects at cell and organelle boundaries. This is particularily true of cells being irradiated by collimated radiation. Moreover, it is known in the art that converging beams, e.g., laser radiation, with a Gaussian intensity profile, become collimated in the focal region due to diffraction and therefore create the "hot spots" in the same manner. The problem with these "hot spots" is that if they coincide in location with the regions of fluorescent material within the cell, then that fluorescent material gives off a high intensity fluorescent signal relative to a low intensity fluorescent signal that the same fluorescent material would have produced if it had not been in the "hot spot". In short, if the "hot spot" is coincident with the fluorescent material, an inaccurate fluorescent reading is obtained.

The flow cytometers of the prior art, upon which the hereinafter described invention improves generally provide multi-parameter detection of stimulated fluorescent light and low-angle forward scatter light. A laser beam normally is used for fluorescence and scatter measurements, with the laser excitation beam being compressed in the direction of the fluid flow by beam shaping optics to achieve a desired thickness at the point of intersection with the particles. These particles are transported in suspension in a jet or flow stream through a measurement region in which the individually isolated particles are illuminated by the line focused or "slit-like" laser beam. The "slit-like" laser beam is used to minimize cell coincidence and to increase laser intensity. These systems use laminar sheath flow techniques for achieving a sequential flow of primarily single cells. Generally, two cylindrical lenses are utilized to create the "slit-like" laser beam, which comprises near-collimated light when impinging upon the particles. Consequently, it has been discovered that the "hot spot" problem previously described is inherent in this prior art design.

In the previously described prior art cytometers, less powerful laser beams lead to cost savings. Hence, it is desirable to provide a cytometer which efficiently uses the near-collimated laser beams commonly found in the prior art cytometers.

It readily can be seen that there is a need in the industry for an improved flow cytometer which more efficiently utilizes the laser beam and which has increased illumination from multiple directions without interfering with the fluorescence and forward scatter light collection.

SUMMARY OF THE INVENTION

The present invention is directed toward an illuminator apparatus and method wherein a source of illumination provides a beam of illuminating radiation which intersects a stream of liquid disposed in a gaseous environment so as to illuminate particles suspended in the stream of liquid. The illuminator apparatus comprises a concave reflector surface having a center of curvature and an optical axis. The optical axis of the concave reflector surface is perpendicularily disposed relative to the stream of liquid and has positioned thereon the beam of illuminating radiation. The stream of liquid defines a cylindrical lens having a focused region of illuminating radiation at the center of curvature of the concave reflector surface. By virtue of this structure, collimated or near-collimated illuminating radiation impinges upon one side of the stream of liquid, undergoes refraction due to the gaseous-liquid interface of the stream, converges to a focus, and thereupon diverges toward the concave reflector surface, reflects from the reflector surface so as to return to the focus, and thereby illuminates the other side of the stream and would illuminate a particle in the stream by both incident and reflected radiation.

BRIEF DESCRIPTION OF THE DRAWINGS

Further objects and advantages of the present invention will become apparent as the following description proceeds, taken in conjunction with the accompanying drawings in which:

FIG. 1 is a front plan view of a first embodiment of the present invention, having a spherical reflector surface;

FIG. 2 is a side plan view of the embodiment shown in FIG. 1;

FIG. 3 is an enlarged partial top view of the embodiment of FIG. 1, as viewed from a horizontal plane;

FIG. 4 is an enlarged partial view of the embodiment of FIG. 1 taken along section line 4—4 of FIG. 3;

FIG. 5 is an enlarged partial view of the embodiment of FIG. 1, as viewed from a vertical plane; and FIG. 6 is an enlarged partial side view of a second embodiment of the present invention, having a cylindrical reflector surface.

DETAILED DESCRIPTION OF THE PREFERRED EMBODIMENT

There is disclosed apparatus means and a method for fluorescent analysis, wherein particles are illuminated from multiple directions, so as to produce resultant fluorescent light, which is subsequently collected. When particles are illuminated by a relatively narrow beam, particle to particle variations cause a spurious spread in the fluorescence measurements which is a function of particle orientation and position and the distribution of the fluorescent materials within the particle and not a function of the amount of fluorescent material within the particle. Consequently, the present invention contemplates providing apparatus means and a method for minimizing the spurious effects of particle-to-particle variations.

There is illustrated in FIGS. 1 and 2 a first embodiment of an illuminator apparatus, generally identified by numeral 10. In this embodiment, the apparatus 10 comprises a reflector 12 having a concave reflector surface 14. The concave reflector surface 14 has the configuration of a partial slice of a sphere. This concave spherical reflector 14 has a focus 16 and a center of curvature 18, both being positioned on an optical axis 20. The apparatus 10 has a particle source (not shown), which provides particles to a jet nozzle 24. The individually isolated particles are entrained in a stream 22 from the jet nozzle 24 through a measurement region 26. The stream 22 comprises a jet or flow stream of liquid having particles, such as biological cells, suspended therein. Hence, this stream 22 provides for the fluid transport of the cells through the measurement region 26, such measurement region being positioned on the optical axis 20 near the center of curvature 18. Ideally, well known laminar sheath flow techniques can be used to confine the particles to the center of the stream 22. More specifically, the particles proceed along the jet stream 22 which is surrounded by sheath liquid. It is important to note that this jet stream 22 has an essentially cylindrical configuration, with a relatively uniform cross sectional configuration in the measurement region 26. The specific construction of the means for transporting the particles through the measurement region 26, in a sequential flow of primarily single cells confined to the center portion of the cylindrically shaped jet stream 22, is of a conventional design well known in the art of flow cytometry.

Referring to FIG. 3, the concave spherical reflector surface 14 is illustrated in an enlarged, top view. The well known geometrical characteristics of spherical reflectors will be herein described. A ray of light which is parallel to the optical axis 20 reflects from the reflector surface 14 so as to be convergent on and pass through the focus 16. Any given ray which impinges upon the reflector surface 14 is reflected so that the angle of incidence is equal to the angle of reflection. Where the oncoming light ray originates from the center of curvature 18, the ray strikes the reflector surface 12 normally and is reflected back along itself so as to return to the focus 16.

As illustrated in FIG. 3, the stream 22, with its cylindrical configuration, acts as a cylindrical lens for illuminating radiation which impinges thereon. The stream 22, in acting as a cylindrical lens, presupposes that the stream 22 is surrounded by a gas so as to define a gaseous-liquid interface. More specifically, the particles are illuminated by illuminating radiation which is ideally laser light. As shown in FIG. 3, the illuminating radiation is nearly parallel or collimated in the plane of the drawing, and could in fact be collimated if desirable. However, merely for the purposes of illustration, a first cylindrical lens 32 is included to make the illuminating radiation slightly convergent, but such a lens is not necessary for the present invention. The illuminating radiation, which strikes the stream 22, passes through the stream, with the exception of that which is reflected, and is refracted so as to converge substantially at a lens focus 34. It should be noted that the more convergent the beam is, the more diffused the light at the focus 34 becomes. Also, imperfections in the configuration of the stream 22 lead to further diffusion of the light at the focus 34. Consequently, it should be appreciated that the focus 34 is not a theoretical point, but is a focal zone. Also, although the illuminating radiation is shown as perpendicularily intersecting the stream 22, some variation from this perpendicular relationship is tolerable. The illuminating radiation passing through the stream 22 substantially converges on this focus 34, so as to pass through the same to diverge.

As depicted in FIG. 3, the illuminating radiation diverges from the focus 34 and reflects from the concave spherical reflector surface 14. The lens focus 34 is positioned to be substantially coincident with the center of curvature 18, as depicted in FIG. 3. By virtue of this coincident relationship, the rays of illuminating radiation diverging from the focus 34 reflect from the spherical reflector surface 14 back along themselves. It should be noted that, as the focus 34 deviates from the position of the center of curvature 18, the diverging illuminating radiation no longer is perfectly normal to the reflector surface 14 when striking the same and consequently the rays do not reflect exactly back along the incoming rays. The greater the deviation the less illuminating radiation that intersects the stream 22 for a second time.

The lens focus was created by refraction of the stream 22. It is this refraction that primarily contributes to the illuminating radiation reflected back on the stream 22. Of lesser importance is the fact that reflection within the stream 22 of the illuminating radiation produces another focus for that illuminating radiation which is reflected. This focus (not shown) is in the vicinity of the lens focus 34, but is more diffuse and does not contribute much to the illumination of the particles. Also, it should be noted that the incident illuminating radiation, which passes the stream 22 without intersecting the same, reflects from the reflector surface 14, and due to being slightly convergent prior to striking the reflector surface 14, converges in a diffused area just short of the focus 16. If only reflection was involved, the illuminating radiation diverging from this diffused area would not intersect with the stream 22. However, this illuminating radiation is sufficiently diffracted inward toward the stream 22 that some of the illuminating radiation makes a minimal contribution to the illumination of the particles.

The object of reflecting the illuminating radiation back on the stream is to further illuminate the particles to eliminate the heretofor described "hot spots" in illumination that create spurious spreads in fluorescence measurement. Consequently, the particles are further illuminated on the side opposite to the side impinged upon by the incident illuminating radiation. Furthermore, this side of the stream 22 is irradiated by divergent radiation, which is better for uniform illumination than collimated radiation.

Up to this point, the illuminating radiation and its reflection from the reflector surface 14 has been described only with respect to the horizontal plane illustrated in FIG. 3. In the embodiment illustrated in FIGS. 3, 4, and 5, the incident illuminating radiation is focused in the vertical plane as illustrated by the cross sectional slit-like configuration 36 of the illuminating radiation in the measurement region 26. This focusing in a vertical plane is accomplished by conventional means, such as a second cylindrical lens 38 shown in FIGS. 3 and 5. As will be discussed hereinafter, the present invention is not limited to focusing the illuminating radiation into the slit-like configuration at the point of intersecting the measurement region 26. However, in this first embodiment of the present invention, the use of a spherical mirror presupposes focusing the illuminating radiation so as to converge the same in the vertical plane illustrated in FIGS. 4 and 5. In other words, the curvature of the reflector surface 14 in the vertical plane compensates for the convergence of the illuminating radiation in the vertical plane of FIG. 5, so as to reflect the illuminating radiation back along the same paths, but in the reverse direction, as the rays of the incoming illuminating radiation. Consequently, the illuminating radiation is reflected back to the focus 34 by the spherical reflector surface 14 both in the horizontal plane as illustrated in FIG. 3 and in the vertical plane as illustrated in FIG. 5. Moreover, this illuminating radiation, upon passing through the region of the focus 34, impinges upon the stream 22 in substantially the same area as the illuminating radiation left the stream 22. The above description presupposes that the cylindrical lens 38 has its focus disposed in coincident relationship with the lens focus 34 and that there is a tolerable amount of refraction of the illuminating radiation in the vertical plane of FIG. 5 as the same passes through the stream 22.

A second embodiment of the present invention is illustrated in FIG. 6, in which the reflector 12 has a concave cylindrical reflector surface 40 with the illuminating radiation being collimated in the vertical plane illustrated in FIG. 6. In general, this embodiment differs from the first embodiment previously described in that the cylindrical lens 38 is not used to converge the illuminating radiation in the vertical plane; hence, the reflector surface 40 does not need any curvature in the vertical plane, as illustrated in FIG. 6. In the first embodiment having the spherical reflector surface 14, the center of curvature 18 was a point. In this second embodiment, the center of curvature, identified by numeral 41, is a line. The difference being that in this second embodiment, the cylindrical reflector surface 40 has no curvature in the vertical plane shown in FIG. 6. Also, it should be noted that in the first embodiment the optical axis 20 is fixed in spacial relationship both in the vertical plane, as shown in FIG. 5, and in the horizontal plane, as shown in FIG. 3. However, from a geometric standpoint, the cylindrical reflector surface 40 has no axial limitation in the vertical plane. However, the optical axis of this second embodiment, identified by numeral 43, is preferably, but not necessarily, centered in bisecting relationship to the reflector surface 40 in the vertical plane as illustrated in FIG. 6. This symmetry of positioning allows for minimizing the width dimension of the reflector surface 40, which results in benefits to be described hereinafter. For the purpose of this description, the width dimension of the reflector surface 14 or 40 is parallel to the flow of stream 22, while the length dimension is perpendicular to the same.

In both of the previously described embodiments, the illuminating radiation, when comprising laser light, has a Guassian profile, so that although the stream 22 intersects only a portion of the width of the laser light, as illustrated in FIG. 3, the greater amount of the laser light is contained in the intersecting portion. Also in both embodiments, the illumination of the particles stimulates emission of fluorescent radiation, including light, which is collected by conventional first detector means 42 shown in FIG. 1.

As previously described, the beam of radiation in the first embodiment is line focused, so as to have a "slit-like" cross section configuration at the point of intersection with the stream 22 of liquid, thereby dictating the spherical reflector surface 14. On the other hand, in the second embodiment, the beam of illuminating radiation is not line focused and therefore comprises essentially collimated radiation at the stream 22 of liquid, just prior to reaching the same. The cross section configuration of this collimated radiation could take any configuration, although it preferably should be circular, ellipsoidal, or another uniform shape in that such shape will in part determine the width and length dimensions of the reflector surface 40. In both embodiments of the reflector surface 14 or 40, the length dimension is substantially greater than the width dimension. The minimizing of the width dimension is of importance in decreasing the blockage of scattered light, as will be described hereinafter. Consequently, it is desirable that the spherical reflector surface 14 has the configuration of a relatively narrow partial slice of a sphere dimensioned and aligned so as to minimize its size, while being large enough to reflect the illuminating radiation passing through and being refracted by the stream 22 of liquid. For the same reasons, it is desirable that the cylindrical reflector surface 40 has the configuration of a relatively narrow partial slice of a cylinder.

The design of the present invention is particularly advantageous when studying small-angle forward light scattering of cells in flow. Objects in flow scatter light as they intersect the laser beam. A second detector means 44, shown in FIG. 2, normally positioned in back of the reflector 12 relative to the stream 22, typically collects the forward light scatter in the 1.0 degree to 19.0 degree range. In that the signal produced is dependent primarily upon the size of the cell, the small angle measurements can be used for size determination or gating. As is apparent from FIGS. 1 and 2, the reflector 12 has a sufficiently small width that the reflector 12 does not significantly interfere with the scattered light. In general, the width dimension of the reflector 12 is approximately equal to the width of the laser beam in the vertical plane as illustrated in FIG. 6, or is less than the width of the incident laser beam, as illustrated in FIG. 5.

Although not illustrated in the drawings, the stream 22 of liquid could be enclosed in a hollow tube having a cylindrical configuration, such tube being preferably, but not necessarily, constructed of glass. As a result, a gas-glass interface and a glass-liquid interface would jointly combine to provide a cylindrical lens.

For the purpose of illustrating the preferred embodiments, the stream 22 of liquid is greatly enlarged relative to the other elements of apparatus 10. Typical horizontal width values of the elements as viewed in the cross section shown in FIG. 4 could be 10 micrometers for the particle diameters, 76 micrometers for the stream 22, 500 micrometers for the laser beam, and 19,000 micrometers for the longitudinal dimension of the reflector surface 14 or 40. These dimensional values are merely illustrative values presented herein only to approximately show the relative dimensional relationships between the elements of the apparatus 10 in one exemplary system in actual use.

It should be noted that by using the same illuminating radiation twice to illuminate the particles, a more efficient utilization of the radiation is accomplished. This more efficient utilization could lead to less expensive laser systems to achieve the same results previously obtainable without the reflector 12.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. In an apparatus for analyzing particles suspended in a liquid of the type having means for providing a substantially cylindrical stream of the liquid and means for impinging the stream with a beam of illuminating radiation to create detectable signals from the particles, the improvement comprising:
   a reflector having a concave reflector surface with an optical axis and a center of curvature;
   said concave reflector surface being arranged to have said optical axis disposed in intersecting relationship with the stream of liquid and to have the beam of illuminating radiation positioned on said optical axis;
   said concave reflector surface being arranged to have said center of curvature positioned substantially at a focus of the stream of liquid, whereby the stream of liquid defines a cylindrical lens having the focus.

2. In the apparatus of claim 1,
   said concave reflector surface comprising a substantially spherical reflector surface;
   said center of curvature substantially comprising a point positioned on said optical axis.

3. In the apparatus of claim 1,
   said concave reflector surface having a configuration of a relatively narrow partial slice of a sphere dimensioned and aligned to receive the illuminating radiation after the illuminating radiation passes through the stream of liquid;
   whereby the illuminating radiation scattered forward after impinging upon the particles may be collected.

4. In the apparatus of claim 1,
   said concave reflector surface comprising a substantially spherical reflector surface;
   the beam of illuminating radiation having a slit-like cross-sectional configuration in the proximity of the stream of liquid, with a substantially smaller width dimension than a length dimension, the width dimension being substantially parallel to the stream of liquid and the length dimension being substantially perpendicular to the stream of liquid;
   said concave reflector surface having a width dimension parallel to the stream of liquid and a length dimension perpendicular to the stream of liquid.

5. In the apparatus of claim 1,
   said concave reflector surface comprising a substantially cylindrical reflector surface;
   said center of curvature substantially comprising a line passing through said optical axis in parallel relationship with the stream of liquid.

6. In the apparatus of claim 1,
   said concave reflector surface having a configuration of a relatively narrow partial slice of a cylinder dimensioned and aligned to receive the illuminating radiation after the illuminating radiation passes through the stream of liquid;
   whereby the illuminating radiation scattered forward after impinging upon the particles may be collected.

7. In the apparatus of claim 1,
   said concave reflector surface comprising a substantially cylindrical reflector surface;
   said concave reflector surface having a width dimension parallel to the stream of liquid and a length dimension perpendicular to the stream of liquid;
   said concave reflector surface having said optical axis substantially positioned in bisecting relationship with respect to said width dimension of said concave reflector surface;
   the beam of illuminating radiation comprising essentially collimated radiation in the proximity of the stream of liquid prior to reaching the same.

8. In a method of analyzing particles wherein the particles suspended in a substantially cylindrical stream of liquid are illuminated by a beam of illuminating radiation to produce detectable optical signals and the illuminating radiation which passes through the stream substantially converges to a focus created by the stream of liquid, the improvement comprising the steps of:
   reflecting the illuminating radiation, passing through the focus from the stream of liquid, off a concave reflector surface, having a center of curvature positioned substantially at the focus, so that the illuminating radiation passes through the focus a second time and diverges to impinge upon the stream of liquid for a second time to further illuminate the particles.

9. In the method of claim 8,
   narrowly confining the configuration of the concave reflector surface in the direction of flow of the stream of liquid, and
   collecting illuminating radiation scattered forward after impinging upon the particles.

10. In the method of claim 8,
    collecting fluorescent radiation stimulated to emission by the illuminating radiation.

* * * * *